United States Patent [19]

Bidan et al.

[11] Patent Number: 5,605,617

[45] Date of Patent: Feb. 25, 1997

[54] CONDUCTIVE POLYMER FILM DOPED BY MIXED HETEROPOLYANIONS USABLE FOR THE DETECTION OF NITRITE IONS, NITROGEN MONOXIDE OR A SUBSTANCE CONTAINING NO

[75] Inventors: Gerard Bidan, Grenoble; Bruno Fabre, Saint-Egreve, both of France; Mieczyslaw Lapkowski, Zabrze, Poland

[73] Assignee: Commissariat a l'Energie Atomique, Paris, France

[21] Appl. No.: 338,616

[22] PCT Filed: Mar. 29, 1994

[86] PCT No.: PCT/FR94/00350

§ 371 Date: Nov. 23, 1994

§ 102(e) Date: Nov. 23, 1994

[87] PCT Pub. No.: WO94/23291

PCT Pub. Date: Oct. 13, 1994

[30] Foreign Application Priority Data

Mar. 29, 1993 [FR] France ................... 93 03588

[51] Int. Cl.$^6$ ................................................ G01N 27/333
[52] U.S. Cl. ..................... 205/781; 204/412; 204/418; 205/780.5
[58] Field of Search ............... 204/153.14, 412, 204/418; 205/780.5, 781

[56] References Cited

U.S. PATENT DOCUMENTS

| | | | |
|---|---|---|---|
| 3,881,997 | 5/1975 | Johnson et al. | 204/153.14 |
| 4,081,345 | 3/1978 | Tolg et al. | 204/153.14 |
| 4,636,314 | 1/1987 | Beuhler et al. | 210/500.25 |
| 4,961,834 | 10/1990 | Kuhn et al. | 204/153.14 |
| 5,190,636 | 3/1993 | Ushizawa et al. | 204/418 |
| 5,264,105 | 11/1993 | Gregg et al. | 204/418 |

FOREIGN PATENT DOCUMENTS 0305769 3/1990 European Pat. Off. .
2625598 7/1989 France .

OTHER PUBLICATIONS

Toth, et al., "Electrocatalytic Reduction of Nitrite and Nitric Oxide to Ammonia With Iron-Substituted Polyoxotungstates", vol. 111, pp. 2444–2451, *Journal of the American Chemical Society*, (1989) month unavailable, Washington, D.C.

Kwok-Keung shiu, et al., "Attempts to Immobilize Catalytically Active Heteropolytungstates On the Surfaces of Electrodes", vol. 309. No. 1 & 2, pp. 115–129, *Journal of Electroanalytical Chemistry and Interfacial Electrochemistry*, Jul. (1991), Lausanne.

*Primary Examiner*—T. Tung
*Attorney, Agent, or Firm*—Burns, Doane, Swecker & Mathis, LLP

[57] ABSTRACT

The invention relates to the amperometric detection of nitrite ions and nitrogen monoxide by electrocatalytic reduction by means of electrodes (15) modified by an electronically conductive polymer film such as poly-(N-methyl pyrrole) doped by mixed heteropolyanions of formulas:

$$[M^{III}X^1W_{11}O_{39}(H_2O)]^{n-} \text{ or}$$

$$[M^{III}X_2^2W_{17}O_{61}(H_2O)]^{7-}$$

in which M represents Fe, Rh, Al, Ga, In or Tl,
 $X^1$ represents P or As and n is equal to 4,
 $X^1$ represents Si or Ge and n is equal to 5, or
 $X^1$ represents B and n is equal to 6, and
 $X^2$ represents P or As.

It also relates to the films and modified electrodes used.

10 Claims, 9 Drawing Sheets

SITES W (2e⁻)
POLY (N-MePy)
$Fe^{III}/Fe^{II}$

CONDUCTIVE POLYMER FILM DOPED BY MIXED HETEROPOLYANIONS USABLE FOR THE DETECTION OF NITRITE IONS, NITROGEN MONOXIDE OR A SUBSTANCE CONTAINING NO

The present invention relates to an electronically conductive polymer film doped by mixed heteropolyanions having a catalytic activity, more particularly for the reduction of nitrite ions to ammonium ions.

More specifically, it relates to the use of electrodes modified by such films for the amperometric detection of nitrite ions and nitrogen monoxide.

Under atmospheric conditions nitrogen monoxide or nitric oxide (of chemical formula NO) is a colourless gas. It differs from nitrous oxide or laughing gas (of chemical formula $N_2O$), which is used as an anasthetic, and from nitrogen dioxide $NO_2$, a reddish gas formed by nitrogen monoxide in the presence of oxygen. The toxicity of nitrogen monoxide results from its free radical structure, one of its unpaired electrons reacting easily. It has been known for some time that bacteria contain nitrogen monoxide, but it was never imagined that said compound exerted essential functions in mammals.

However, roughly 7 years ago studies in various fields of biology converged to reveal the biological importance of nitrogen monoxide. Nowadays the latter appears as an essential biological carrier enabling the white corpuscles to destroy tumour cells and bacteria and enabling neurotransmitters to dilate blood vessels.

In addition, nitrogen monoxide is an interneuronal carrier in the brain and in other regions of the body. It could belong to a new family of neurotransmitters differing very significantly from all known neurotransmitters. The explanation of its action procedure, its distrbution in the organism and its interactions with other biomolecules is opening new windows in connection with the operation of the memory and with respect to the treatment of neurodegenerative diseases (S. Snyder and D. Bredt, Pour la Science, no.177, 1992, p.70). The detection of this molecule named "molecule of the year 1992" by the journal Science, vol.258, p.1862 consequently has a considerable interest.

Nitrite ions occur in our natural environment and are widely involved in the preservation of foods. It is also of interest to have methods for detecting these ions, which are not only sensitive and precise, but also simple and fast, because the reaction of nitrites with most aliphatic and aromatic amines leads to the formation of N-nitrosamines, whereof a large number are recognized as having a significant cancerigenic power.

The known processes for the detection of nitrite ions present in a solution call on spectrophotometric, fluorometric or chromatographic methods, as described by Nakamura et al in Analytical Letters, 16 (A11), 1983, pp.811–819; by Ohta et al in Anal. Chem., 1986, 58, pp.3122–3135; and by Verma in Anal. Letters 25 (11), 1992, pp.2083–2093.

Electrochemical detection processes of nitrite ions by polarography based on the reaction of $NO_2^-$ with sulphanilic or orthanilic acid, or on the reduction of $NO_2^-$ to NO and then its reaction with diphenylamine are also known and are described by Sulaiman in Anal. Chem., 1984, 56, pp.2405–2407 and by Holak et al in Anal. Chem., 1992, 64, pp.1313–1315.

Processes are also known for the detection of nitrite ions which use selective electrodes based on cobalt porphyrin or vitamin B12, as described by Li et al in Anal. Chem., 1991, 63, pp.2168–2174 and by Daunert et al in Anal. Chem., 1989, 61, pp.499–503.

Among these processes, great interest is attached to chromatographic processes because they have a good sensitivity. However they are difficult to carry out and the costs involved are high.

Spectrophotometric processes are very sensitive and very selective, but require a strict control of the pH and temperature. Moreover, the results can be disturbed by the presence of certain ions such as heavy metal ions and $Cu^{2+}$, $Fe^{3+}$ and $I^-$.

Electrochemical processes using selective electrodes suffer from the disadvantage of a long response time and also give rise to interference with certain ions. such as $NO_3^-$ and thiocyanate ions.

Recently research has been carried out on other processes for the detection of nitrite ions, in particular amperometry. Thus, Younathan et al in Inorg. Chem., 1992, 31, pp.3280–3285 suggests the use of electrodes modified by a polymer film based on iron porphyrin for the detection of nitrite ions by electrochemical reduction catalyzed by iron porphyrin.

However, such electrodes are not completely satisfactory because the reduction of $NO_2^-$ catalyzed by these porphyrins leads to the formation of numerous secondary products such as ammonia, nitrous oxide, nitrogen and hydroxylamine. Moreover, the Fe(III) form of iron porphyrins is sensitive to NO and can react therewith and these electrodes can be rapidly deactivated.

Doherty and Vos in J. Chem. Soc. Faraday trans., 1992, 88 (19), pp.2903–2907 have used electrodes modified by other polymers for the electrocatalytic reduction of nitrite ions, but the polymer used swells when it is immersed in an electrolyte, which can lead to its detachment and makes it difficult to use in the nitrite ion detection process.

The present invention specifically relates to electronically conductive polymer films doped by mixed heteropolyanions having catalytic properties for the reduction of nitrite ions, nitrogen monoxide and substances containing NO, which have the advantage of a high chemical resistance, of being stable, of being sensitive solely to nitrite ions and NO and of permitting their dosing with a short response time.

The invention therefore relates to electronically conductive polymer film doped by mixed heteropolyanions complying with one of the formulas:

and in which M represents Fe, Rh, Al, Ga, In or Tl,
$X^1$ represents P or As and n is equal to 4,
$X^1$ represents Si or Ge and n is equal to 5, or
$X^1$ represents B and n is equal to 6, and
$X^2$ represents P or As.
provided that $X^1$ does not represent Si when M represents Fe.

These mixed heteropolyanions are known as catalysts for the conversion of nitrite ions into ammonia, as described by Toth et al in J. Am. Chem. Soc., 1989, 111, pp.2444–2451, but their catalytic activity in the form of dopant ions incorporated into an electronically conductive polymer has not been demonstrated and their use for the detection of nitrite ions has also not been envisaged by these authors.

Shiu et al, J. Electroanal. Chem., 309, 1991, pp.115–129 attempted to use the mixed heteropolyanion $FeSiW_{11}O_{39}$ for the catalytic reduction of $H_2O_2$ after incorporating it into a conductive polymer constituted by polypyrrole, but they found that the polypyrrole was rapidly degraded during said use and was therefore incapable of retaining the heteropolyanion in a form usable for catalysis.

However, according to the present invention, it has been found that conductive polymer films containing mixed heteropolyanions could be effectively used for the electrocatalytic reduction of nitrite ions for a prolonged period of time without any loss of their catalytic properties.

It has also been found that the reduction of NO can be catalyzed and performed in reproducible manner by the mixed heteropolyanions of the present invention. The immobilization of such a catalyst in an electronically conductive polymer matrix on the surface of a vitreous carbon electrode is particularly interesting, because the thus modified electrode constitutes a nitrogen monoxide-sensitive system. The latter can in fact be detected electrochemically, by reduction in a slightly acid medium, which leads to the formation of the ions:

$$NH_4^+(NO+5e^-+6H^+ \rightarrow NH_4^+ + H_2O).$$

The polymers used in these films are generally conjugate polymers such as polymers of pyrrole, thiophene, aniline and their derivatives. Examples of such polymers are polypyrrole and poly-(N-alkyl pyrrole) such as poly-(N-methyl pyrrole).

The heteropolyanions used in these films can be prepared and characterized using the methods described by Zonnevijlle et al in Inorg. Chem., 21, 1982, pp.2742–2757.

Such electronically conductive polymer films incorporating mixed heteropolyanions can be prepared by electropolymerization using the process described in FR-A-2 625 598.

According to this process, the polymerization of a precursor monomer of the electronically conductive polymer takes place in a solution containing a compound of the mixed heteropolyanion having one of the aforementioned formulas.

Preferably, polymerization takes place by the electrochemical oxidation of the precursor monomer using as the mixed heteropolyanion compound the corresponding acid or a salt complying with one of the formulas:

$$A_n[M^{III}X^1X_{11}O_{39}(H_2O)]^{n-} \text{ and}$$

$$A_{7M}{}^{III}X_2^2W_{17}O_{61}(H_2O)]^{7-}$$

in which A represents $Na^+$, $H^+$, $K^+$, $NH_4^+$ or a quaternary ammonium ion of formula $NR_4^+$, in which the R's, which can be the same or different, are alkyl or aryl groups.

In this process, it is possible to use aqueous solutions or organic solutions or use the mixed heteropolyanion compound as the electrolyte. The choice of solution more particularly depends on the precursor monomer used. Electrochemical oxidation is carried out by applying a potential difference between two electrodes immersed in the solution. This makes it possible to directly form on one of the electrodes an electronically conductive polymer deposit doped by the mixed heteropolyanions, whose thickness depends on the duration of application of the potential difference.

For applying said potential difference, it is possible to operate in two different ways:

a) either carry out a linear potential scan between two terminals, whereof one is close to the monomer oxidation start potential, or b) perform electrolysis at an imposed potential or current.

In both cases, a conductive polymer is obtained incorporating in general 0.04 to 0.12 mixed heteropolyanion per monomer unit. The electrode coated with such a polymer film can be used as the electrode for the detection of $NO_2^-$ ions, nitrogen monoxide or a substance containing a NO group by an amperometric process.

The invention also relates to an electrode for the detection of $NO_2^-$ ions, nitrogen monoxide or a substance containing a NO group, which comprises an electrically conductive support covered by an electronically conductive polymer film doped by mixed heteropolyanions complying with one of the formulas $$[M^{III}X^1W_{11}O_{39}(H_2O)]^{n-} \text{ and}$$

$$[M^{III}X_2^2W_{17}O_{61}(H_2O)]^{7-}$$

in which M represents Fe, Rh, Al, Ga, In or Tl,
$X^1$ represents P or As and n is equal to 4,
$X^1$ represents Si or Ge and n is equal to 5, or
$X^1$ represents B and n is equal to 6, and
$X^2$ represents P or As.

The support of said electrode can be made from various electricity-conducting and optionally optically transparent materials. Preferably use is made of an electrode support made from vitreous carbon or a carbon felt, when the electrode is to be used for amperometric dosing.

However, it is also possible to use optically transparent supports, e.g. formed from conductive deposits on glass or transparent plastic when the electrode is to be used for spectrophotometric dosing.

Preferably, the polymer is poly-(N-methyl pyrrole) and the mixed heteropolyanion is $[Fe^{III}PW_{11}O_{39}(H_2O)]^{4-}$.

According to the invention, it is possible to use the electrode coated with such a polymer film incorporating mixed heteropolyanions for the detection of nitrite ions by amperometry.

The invention also relates to a process for the amperometric detection of nitrite ions, nitrogen monoxide or a substance containing a NO group present in a sample, which consists of carrying out an electrocatalytic reduction of the nitrite ions, nitrogen monoxide or substance containing a NO group present in said sample by means of the electrode described hereinbefore and measuring the catalytic current accompanying said reduction.

Preferably, the electrocatalytic reduction takes place in a medium buffered to a pH of approximately 4.6.

According to the invention, a sensor for the detection of nitrite ions, nitrogen monoxide or a substance containing a NO group for performing said process comprises a tight enclosure containing an aqueous solution, three electrodes respectively constituted by a first $NO_2^-$ ion detection electrode according to the invention, a second auxiliary electrode and a third reference electrode, immersed in the aqueous solution, means for introducing a sample to be dosed in said aqueous solution, means for applying a potential difference between the first and third electrodes and means for measuring the intensity of the electric current flowing between the first and second electrodes.

In said sensor, the amperometric detection of the nitrite ions, nitrogen monoxide or NO group is based on the measurement of the catalytic current accompanying the reduction of the $NO_2^-$ ions or NO to $NH_4^+$ ions when the catalyst is constituted by the mixed heteropolyanion immobilized in the electronically conductive polymer. The catalytic current is the difference of the peak currents at the potential at which catalysis occurs, in the presence and absence of nitrite ions. This catalytic current increases with the nitrite ion concentration, but is also dependent on the catalyst quantity immobilized in the conductive polymer and therefore the thickness of the deposit on the electrode. For a given nitrite ion concentration, there is an optimum thickness making it possible to have a maximum catalytic response.

The thickness of the conductive polymer deposit doped by the mixed heteropolyanions is directly linked with the charge accumulated during the synthesis of the polymer, which is easily measurable by a coulomb meter.

Preferably, use is made of electrodes in which the electronically conductive film doped by the mixed heteropolyanions has a thickness of 0.1 to 1 μm, which corresponds to an accumulated charge of 50 to 150 mC/cm$^2$ of electrode.

During the electrocatalytic reduction, the $NO_2^-$ ions react with reduced forms of the mixed heteropolyanion immobilized in the conductive polymer to form a complex of the nitrosyl type $[Fe^{II}(NO)XW_{11}O_{39}]^{(n+1)-}$ which can be revealed by visible spectrophotometry, the maximum absorption being at 460–470 nm. The reaction process is as follows:

The $NH_4^+$ ions are formed when the nitrosyl complex is reduced to $[Fe^{II}(NH_3)XW_{11}O_{39}]^{(n+2)-}$. The mechanism of this catalytic reduction of the $NO_2^-$ ions to $NH_4^+$ ions can be represented in the following way:

A nitrite ion sensor operating according to this principle has numerous advantages compared with other nitrite ion measuring sensors.

Firstly, the presence of mixed heteropolyanions serving as a catalyst makes it possible to produce in preponderant manner $NH_4^+$ ions, whereas with other catalysts used for the reduction of nitrite ions, such as iron porphyrins, polypyridyl complexes of ruthenium and osmium, secondary products such as hydroxylamine are formed in a non-negligible quantity. Moreover, the Fe(III) form of the iron porphyrins can react with NO to form a nitrosyl complex, whereas the mixed heteropolyanion does not react with NO. In the same way, the Fe(II) form of the iron porphyrins can react with CO.

The mixed heteropolyanions used as catalysts in the invention are consequently more inert than iron porphyrins with respect to certain compounds liable to poison the catalyst. This feature is also retained when they are immobilized in matrixes of electronically conductive polymers.

Compared with chromatographic processes for the detection of nitrite ions, the sensor according to the invention is of interest because it is completely competitive with such processes as regards cost, simplicity and sampling time.

Compared with spectrophotometric processes, the sensor according to the invention is of interest because such processes are very sensitive in general and are often disturbed by interference problems and are dependent on the toxicity of the reagents used, which is not the case with the sensor according to the invention.

Compared with selective electrodes, the sensor according to the invention is advantageous, because there is no need to use a hydrophobic agent for immobilizing the catalyst in an irreversible manner in the conductive polymer matrix. In addition, the response time of the sensor is much shorter than that of selective electrodes and its response is not modified by the presence of certain $NO_3^-$ ions, which are the main interfering ions in selective electrodes. Finally, the sensor according to the invention has a virtually unlimited life if it is snored in an aqueous solution buffered to a pH of 4.6, which is not the case with selective electrodes which have a relatively limited life.

The nitrite ion sensor according to the invention can be used in various fields, e.g. in the medical field for the dosing of nitrite ions in urine, saliva, etc.; in the food field for the dosing of nitrite ions in meat, fish and fruit; in the agricultural field for the dosing of nitrite ions in fertilizers, nutrient compounds, vegetation, etc.; and in the water treatment field for checking the content of nitrite ions in natural water, drinking water, sea water and industrial water.

Other features and advantages of the invention can be gathered from reading the following examples given in an illustrative and non-limitative manner with reference to the attached drawings, wherein show.

EXAMPLE 1

Preparation of a Vitreous Carbon Electrode Covered With a Polypyrrole Film Doped By $[Fe^{III}PW_{11}O_{39}(H_2O)]^{4-}$ a) Preparation of the $[(C_4H_9)_4N]_4[Fe^{III}PW_{11}O_{39}(H_2O)]$, $7H_2O$ Salt.

This preparation takes place using the process described by Zonnevijlle et al, Inorg. Chem., 21, p.2751, 1982.

65.97 g ($2 \cdot 10^{-1}$ mole) $Na_2WO_4$, $2H_2O$ and 6.91 g ($1.82 \cdot 10^{-2}$ mole) of $Na_3PO_4$, $12H_2O$ are added to 100 ml of water. The solution is heated to 80° C. and to it are then slowly added 27.4 ml of 37% HCl, whilst ensuring that the pH still exceeds 3 in order to prevent the degradation of $PW_{11}O_{39}^{7-}$ to $PW_{12}O_{40}^{3-}$ and in this way the $Na_2PW_{11}O_{39}$ salt is obtained. The soluton is then heated to 95° C. and to it are added in the form of small portions 7.49 g ($1.85 \cdot 10^{-2}$ mole) of $Fe(NO_3)_3$, $9H_2O$, namely in a 2% excess compared with the stoichiometric quantity, in order to obtain the $[Fe^{III}PW_{11}O_{39}(H_2O)]^{4-}$ sodium salt. The solution becomes yellow-orange, then maroon and cloudy. It is kept at 95° C. for 15 min at the end of addition and is then filtered hot to recover the excess iron which has precipitated in the form $Fe(OH)_3$ and the filtrate is allowed to cool in air to ambient temperature. To the filtrate are then added 23.6 g ($7.27 \cdot 10^{-2}$ mole) of $[(C_4H_9)_4N]Br$ (99%) in small portions. A yellow precipitate appears which is recrystallized in hot water and dried in an oven at 90° C. for two days.

This gives the $[(C_4H_9)_4N]_4 [Fe^{III}PW_{11}O_{39}(H_2O)]$, $7H_2O$ with a 65% yield.

b) Electrochemical Synthesis of the Polypyrrole Doped By $(Fe^{III}PW_{11}O_{39}(H_2O))^{4-}$.

Preparation takes place of a solution at $5 \cdot 10^{-2}$ mole/l of the $[(C_4H9)_4N]_4 [Fe^{III}PW_{11}O_{39}(H_2O)]$, $7H_2O$ salt and at $10^{-2}$ mole/l of the pyrrole in acetonitrile. This solution is introduced into a 10 ml cell having an arrangement with three electrodes, including a vitreous carbon working electrode with a surface of 0.07 cm$^2$, at $10^{-2}$M Ag/Ag$^+$ reference electrode and a platinum counterelectrode, as well as a potentiostat. The working electrode is raised to a potential of 0.70 V compared with the reference electrode for a time such that 8 mC or 114 mC/cm$^2$ of electrode pass into the circuit. On the working electrode is then formed a deposit of polypyrrole doped by the mixed heteropolyanion $[Fe^{III}PW_{11}O_{39}(H_2O)]^{4-}$. The electrode is then washed with acetonitrile for 2 min and then with water for 2 min.

EXAMPLE 2

Preparation of a Vitreous Carbon Electrode Modified By a Polypyrrole Deposit Doped By $[Fe^{III}PW_{11}O_{39}(H_2O)]^{4-}$ In this example, polypyrrole deposition takes place using an aqueous solution containing on the one hand the sodium salt of the heteropolyanion and on the other pyrrole.

a) Preparation of the Sodium Salt of the Heteropolyanion.

The same operating procedure as in example 1a) is followed for obtaining the $Na_7PW_{11}O_{39}$ salt, then to it is added $Fe(NO_3)_3$, $9H_2O$ as in example 1a) in order to form the $[Fe^{III}PW_{11}O_{39}(H_2O)]^{4-}$ sodium salt. After elimination by filtration of the excess iron which has precipitated half the water is evaporated and then the solution which has become cloudy is cooled to ambient temperature. It is then fractionated and to each fraction is added methanol in order to precipitate the sodium salt. A vacuum evaporation followed by a filtration of each fraction makes it possible to recover the sodium salt which is then dried in vacuo at 60° C. for one day. This gives said sodium salt with a 25% yield. The formula of this salt is deduced from the elementary analysis and is $Na_4 [Fe^{III}PW_{11}O_{39}(H_2O)]$, $13H_2O$.

b) Synthesis of the Polypyrrole Doped By $[Fe^{III}PW_{11}O_{39}(H_2O)]^{4-}$.

In order to carry out this synthesis, the starting product is an aqueous solution at $5 \cdot 10^{-2}$ mole/l of the sodium salt previously obtained and at $10^{-2}$ mole/l of pyrrole and said solution is introduced into a 10M cell having an arrangement with 3 electrodes, as in example 1. This is followed by doped polypyrrole deposition by cyclic voltamperometry with a scanning speed of 20 mV/s at between −0.6 and +0.6 V, where oxidation of the pyrrole to form the polymer is possible. Thus, on the vitreous carbon electrode is formed a polypyrrole deposit doped by the mixed heteropolyanion $[Fe^{III}PW_{11}O_{39}(H_2O)]^{4-}$. The said electrode is then washed with water for 2 min.

Its behaviour is then studied in cyclic volt-amperometry at 10 mV/s in 20 ml of an aqueous solution buffered to pH=4.6 with 0.1 mole/l of $CH_3COOH$ and 0.1 mole/l of $CH_3COONa$.

Figure 1:
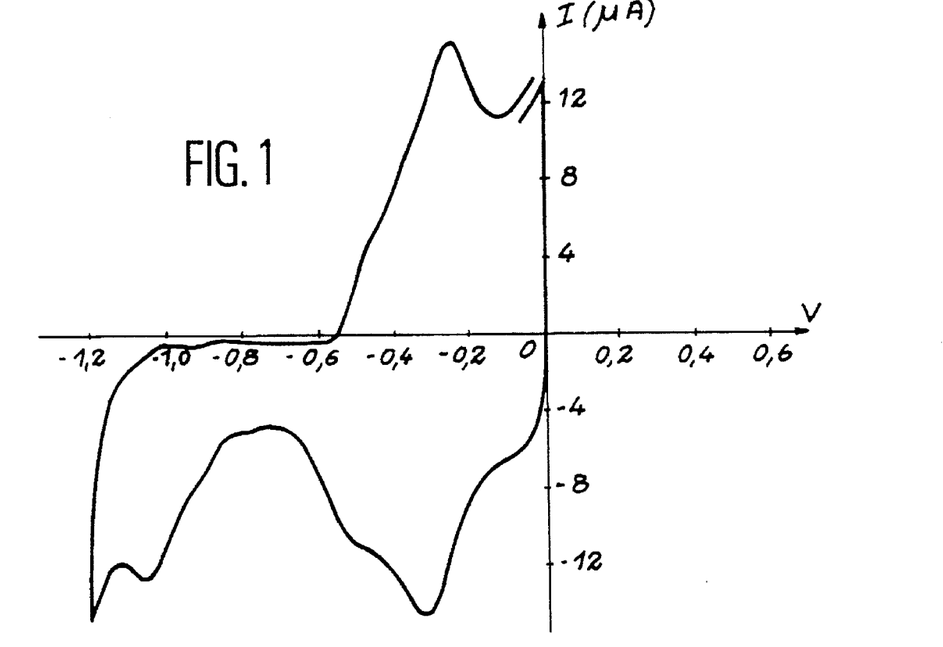
FIGS. 1 and 2 Volt-amperograms obtained with the electrodes prepared in examples 2 and 5.

FIG. 1 is the volt-amperogram obtained at between −1.25 and 0 V. On this volt-amperogram it is possible to see the reversible, bielectronic charge transfers from the tungsten sites of the mixed heteropolyanion immobilized at −1.10 and −0.93 V respectively, as well as the $Fe^{3+}/Fe^{2+}$ charge transfer at −0.28 V. The electroactivity of the polypyrrole matrix is masked by the latter transfer. Although the medium is acid, there is no reduction of protons in the negative range due to the high overvoltage of the protons on the vitreous carbon and the difficulty which the latter can have in diffusing into the polymer, whereas there would be a release of hydrogen as from weak negative potentials with a platinum working electrode, which only has a low overvoltage on hydrogen discharge.

At the end of 5 cycles, the modified electrode has reached its electrochemical stability, which is indispensable for its use for detecting nitrite ions by catalytic reduction.

Examination then takes place of the effect of the addition of nitrite ions to the buffered aqueous solution on the volt-amperogram obtained after stopping the electrode potential at 0 V. To this end, using a microsyringe a certain quantity of $NaNO_2$ dissolved in the same aqueous solution buffered to pH=4.6 is added and then electrolysis is continued at 0 V for 1 min, so that the ions diffuse into the entire solution. After 1 min, scanning resumes at 10 mV/s towards negative potentials up to −1.25 V and the catalytic current accompanying the reduction of the $NO_2^-$ ions to $NH_4^+$ ions is measured at −1.20 V. Once the potential reaches −1.25 V, scanning is continued in the opposite direction to 0 V, where addition takes place of a supplementary quantity of nitrite ions in the same buffered aqueous solution.

The measured catalytic current rises linearly with the concentration of the nitrite ions in the range $10^{-4}$ to $3 \cdot 10^{-2}$M. Below $10^{-4}$M, it is no longer possible to precisely measure the currents which are approximately 1/50 nA. Above $3 \cdot 10^{-2}$M, the variation of the current intensity as a function of the concentration of nitrite ions is no longer linear.

The polypyrrole deposit doped by said mixed heteropolyanion having a thickness corresponding to an accumulated charge of 8 mC, therefore has a very good catalytic activity with respect to the reduction of $NO_2^-$ ions.

It has been shown that deposits obtained using other charges for the synthesis give lower catalytic currents.

EXAMPLE 3

Preparation of a Vitreous Carbon Electrode Modified By a Polypyrrole Deposit Doped By $[Fe^{III}PW_{11}O_{39}(H_2O)]^{4-}$ This example follows the same operating procedure as in example 2 for depositing the polypyrrole film doped by the mixed heteropolyanion, but electropolymerization takes place by electrolysis, instead of cyclic voltamperometry, by raising the vitreous carbon electrode to 0.65 V until 8 mC (i.e. 114 mC/cm$^2$) of electrode pass into the circuit.

Under these conditions, a doped polypyrrole deposit is obtained and the electrode has the same characteristics as in example 2. It is also pointed out that the electrode of example 1 has the same characteristics.

EXAMPLE 4

Preparation of an Electrode Modified By a Polyaniline Film Doped By $[Fe^{III}PW_{11}O_{39}(H_2O)]^{4-}$ In this example, preparation firstly takes place of the sodium salt of the heteropolyanion as in example 2, followed by the dissolving of 3 g (9.7·10$^{-4}$ mole) of said Na$_4$[Fe$^{III}$PW$_{11}$O$_{39}$(H$_2$O)],13H$_2$O salt in 20 ml of water and then the solution is made to circulate over a cation exchange resin having a nominal capacity of 5 meq/g of dry resin, which has been conditioned beforehand with approximately 10% HCl. Thus, a solution is recovered containing 9.7·10$^{-4}$ mole of H$_4$[Fe$^{III}$PW$_{11}$O$_{39}$(H$_2$O)] in 27 ml of water, i.e. a concentration close to 3.5·10$^{-2}$ mole/l and to this solution is added aniline with a concentration of 5·10$^{-2}$ mole/l.

This is followed by the electrochemical synthesis of the polyaniline on a vitreous carbon electrode using the same cell as in examples 1 to 3 and on raising the vitreous carbon electrode to a potential of 1.1 V.

The study of the behaviour of this electrode in cyclic voltamperometry at 10 mV/s indicates a transfer of the tungsten sites of the mixed heteropolyanion immobilized at −1.10 and −0.90 V and a DE Fe$^{3+}$/Fe$^{2+}$ transfer, but the latter disappears after two cycles. Therefore this modified electrode has a lower stability than that of electrodes modified by polypyrrole films.

EXAMPLE 5

Preparation of a Vitreous Carbon Electrode Modified By a Poly-(N-Methyl Pyrrole) Film Doped By $[Fe^{III}PW_{11}O_{39}(H_2O)]$ The same operating procedure as in example 1 is followed for depositing a poly(N-pyrrole) film doped by said mixed heteropolyanion, except that the acetonitrile solution contains 10$^{-2}$ mole/l of N-methyl pyrrole instead of 10$^{-2}$ mole/l of pyrrole. Electropolymerization takes place in the potentiostatic mode raising the vitreous carbon electrode to a potential of 0.60 V compared with the 10$^{-2}$M Ag/Ag$^+$ electrode until 8 mC or 114.3 mC/cm$^2$ of electrode pass into the circuit.

This gives a vitreous carbon electrode modified by a poly-(N-methyl pyrrole) film doped by the heteropolyanion $[Fe^{III}PW_{11}O_{39}(H_2O)]^{4-}$ containing 0.06 to 0.08 ion per unit (N-methyl pyrrole).

The thus obtained modified electrode is washed with acetonitrile for 2 min and then with water for 2 min and is then immersed in 20 ml of an aqueous solution buffered to pH=4.6 with 0.1M CH$_3$COOH and 0.1M CH$_3$COONa, in order to study the electrochemical behaviour of said electrode by cyclic voltamperometry at between −1.25 and 0 V with a scanning speed of 10 mV/s.

Figure 2:
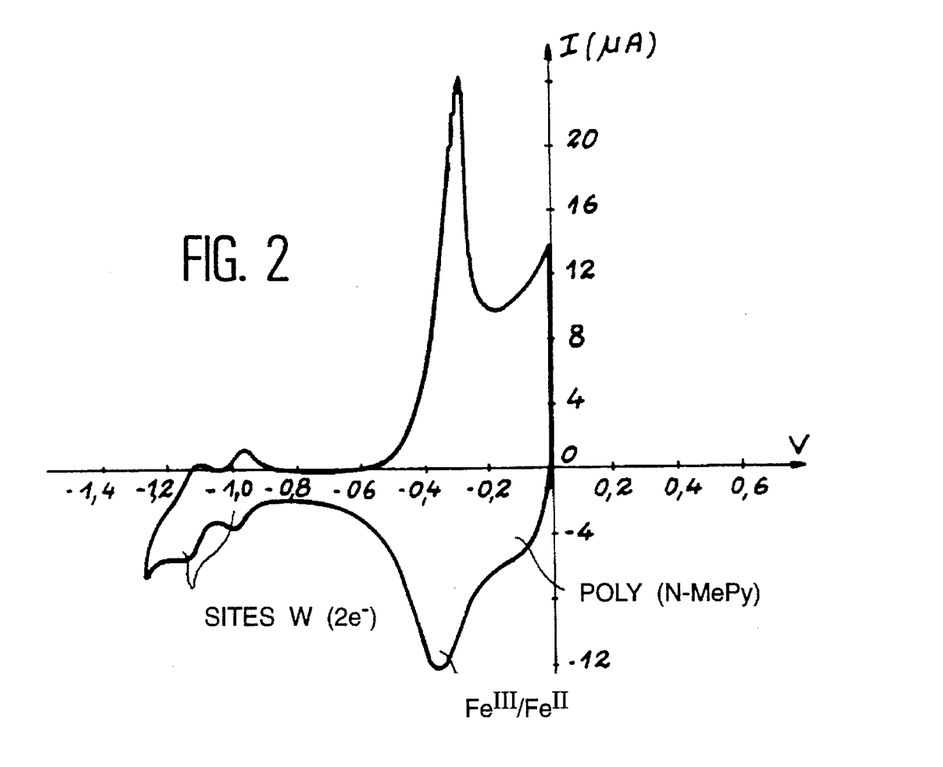

FIG. 2 shows the volt-amperogram obtained under these conditions, where it is possible to see the reversible electronic transfers of the tungsten sites at −1.10 V and −0.94 V, the Fe$^{3+}$/Fe$^{2+}$ pair at −0.32 V for the mixed heteropolyanion and the redox exchange of the polymer matrix. The electrochemical stability of the electrode is reached after 5 cycles and it is then possible to use the modified electrode for the detection of nitrite ions by catalytic reduction.

EXAMPLES 6 TO 12

Vitreous Carbon Electrode Modified By a Poly-(N-Methyl Pyrrole) Film Doped By $[Fe^{III}PW_{11}O_{39}(H_2O)]^{4-}$ These examples follow the same operating procedure as in example 5 for depositing a poly-(N-methyl pyrrole) film doped by the same heteropolyanion, but electrolysis is carried out by passing into the circuit different synthesis charges and respectively 1 mC (14.3 mC/cm$^2$ of electrode ) in example 6,
2 mC (28.6 mC/cm$^2$ of electrode) in example 7,
4 mC (57.1 mC/cm$^2$ of electrode) in example 8,
6 mC (85.7 mC/cm$^2$ of electrode) in example 9,
10 mC (142.9 mC/cm$^2$ of electrode) in example 10,
12.5 mC (178.6 mC/cm$^2$ of electrode) in example 11, and
15 mC (214.3 mC/cm$^2$ of electrode) in example 12.

The films obtained contain substantially the same quantity of heteropolyanions, namely 0.06 to 0.08 $[Fe^{III}PW_{11}O_{39}(H_2O)]^{4-}$ per unit (N-methyl pyrrole).

EXAMPLE 13

Use of the Film of Example 8 For Detecting Nitrite Ions

Figure 3:
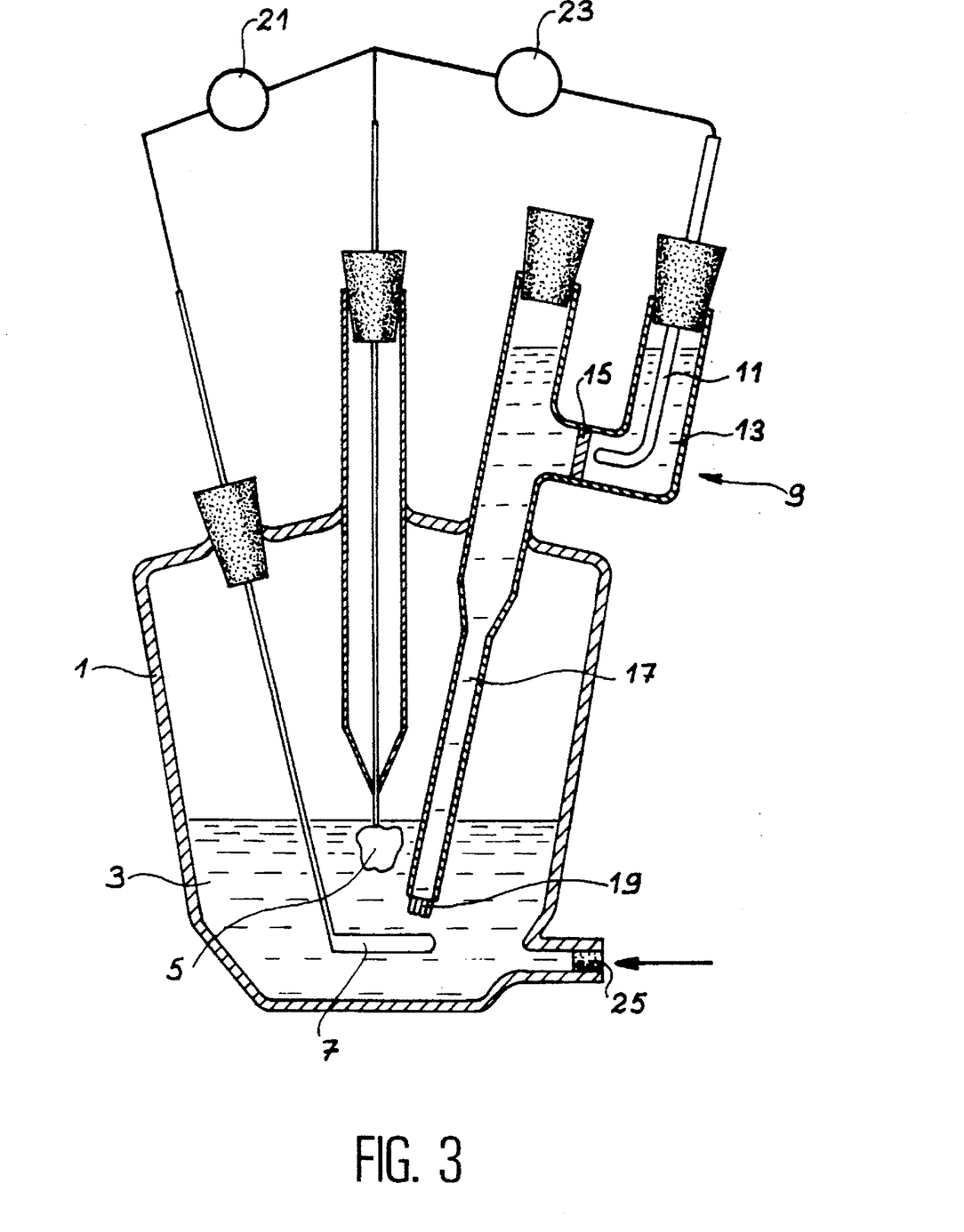
FIG. 3 A diagrammatic representation of a sensor for the detection of nitrite ions according to the invention.

The example uses the electrode obtained in example 8, which corresponds to a charge for the synthesis of the film of 4 mC or 57.1 mC/cm$^2$ of electrode for detecting nitrite ions. A sensor suitable for this detection is illustrated in FIG. 3. FIG. 3 shows that the sensor comprises a tight enclosure (1) containing an aqueous solution (3) constituted in this case by a solution buffered to pH=4.6 containing 10$^{-1}$ mole/l of CH$_3$COOH and 10$^{-1}$ mole/l of CH$_3$COOH and 10$^{-1}$ mole/l of CH$_3$COONa.

A first electrode (5) constituted by the modified electrode obtained in example 5, a second electrode (7) constituted by a platinum electrode and a third reference electrode (9) are immersed in the aqueous solution (3).

The reference electrode (9) is a 10$^{-2}$M Ag/Ag$^+$ electrode comprising a silver wire (11) immersed in an acetonitrile solution (13) containing 10$^{-1}$ mole/l of LiClO$_4$ and 10$^{-2}$ mole/l of Ag NO$_3$ in contact by a sintered member (15) with an acetonitrile solution (17) containing 10$^{-1}$ mole/l of LiClO$_4$, itself in contact by a second sintered member (19) with the aqueous solution (3).

The electrodes (5) and (7) are connected by an external circuit incorporating an ammeter (21) and the electrodes (5) and (9) are interconnected by a circuit incorporating means (23) for applying a potential difference. The sample to be dosed can be introduced into the solution (3), e.g. using a microsyringe, through the opening (25).

After subjecting the electrode (5) to five electrochemical cycles at between −1.25 V and 0 V, as in example 5, the potential of the electrode is stopped at 0 V and by means of the opening (25) addition takes place to the sensor of a certain amount of $NaNO_2$ dissolved in the same buffered aqueous solution as in solution (3) for studying the influence of this addition on the voltamperogram obtained at 10 mV/s and these additions are repeated in order to obtain voltamperograms with total concentrations of nitrite ions in said sensor of 0.5, 1, 2, 5 and 10 mmole/l.

Figure 4:
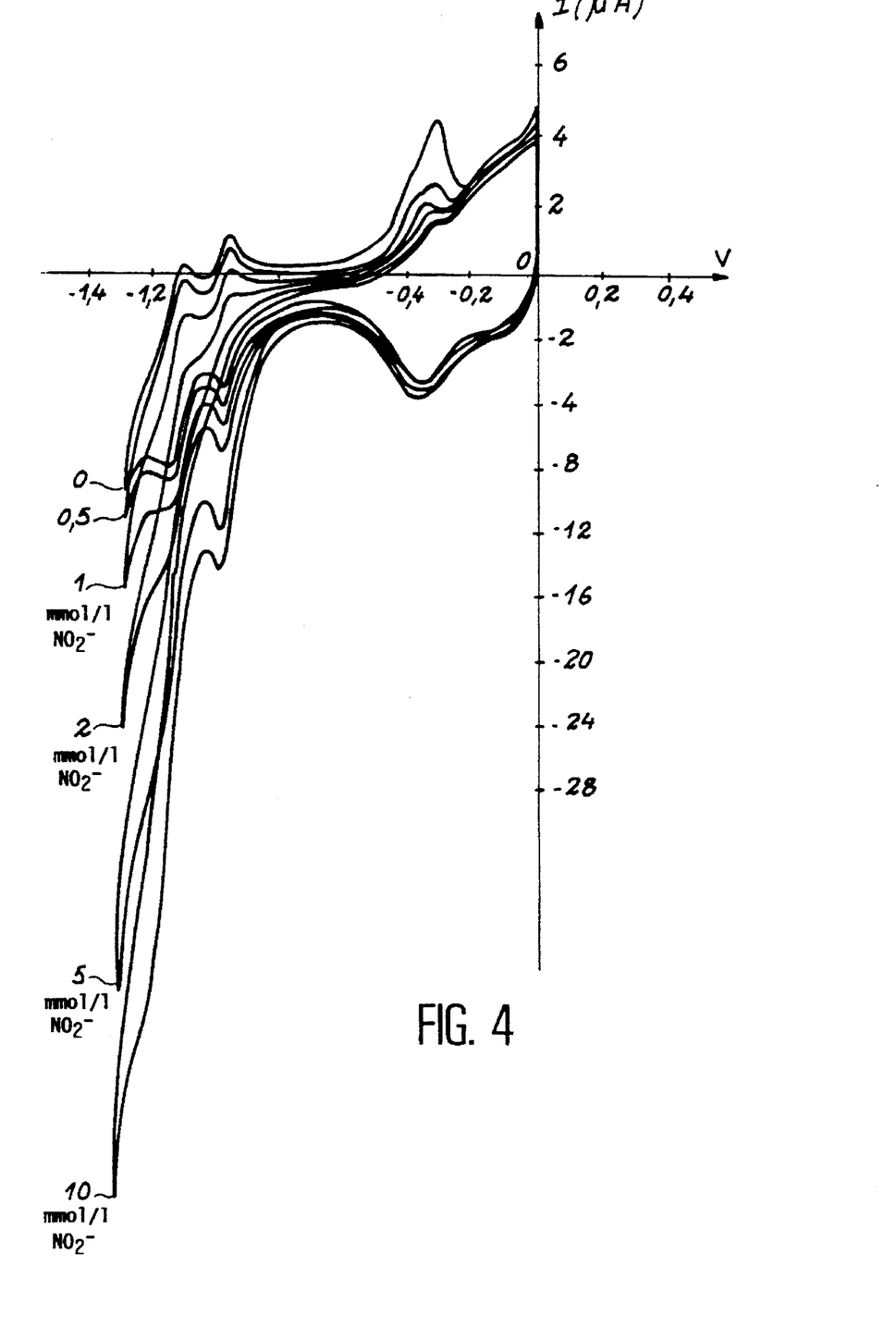
FIG. 4 The volt-amperogram obtained with the electrode of example 5 in the presence of nitrite ions.

FIG. 4 illustrates the volt-amperograms obtained under these conditions and it can be seen that there is a significant increase of the reduction current as a function of the added nitrite ion quantity. This reduction current increase with the concentration of the nitrite ions is easily explainable by the electrocatalysis reaction mechanism.

Thus, in the film $[Fe^{III}PW_{11}O_{39}(H_2O)]^{4-}$ serves as the catalyst and the added nitrite ions $NO_2^-$ react with the reduced form of the catalyst in order to form a complex of the nitrosyl type: $[Fe^{II}(NO)PW_{11}O_{39}]^{5-}$, which can be observed by visible spectrophotometry when the electrode on which is deposited the poly-(N-methyl pyrrole) film is optically transparent. With such an electrode, it is possible to show this complex at 465 nm on maintaining the electrode at the reduction potential of the catalyst, i.e. at the potential of the cathode peak of $Fe^{3+}/Fe^{2+}$, which −0.32 V.

Figure 5:
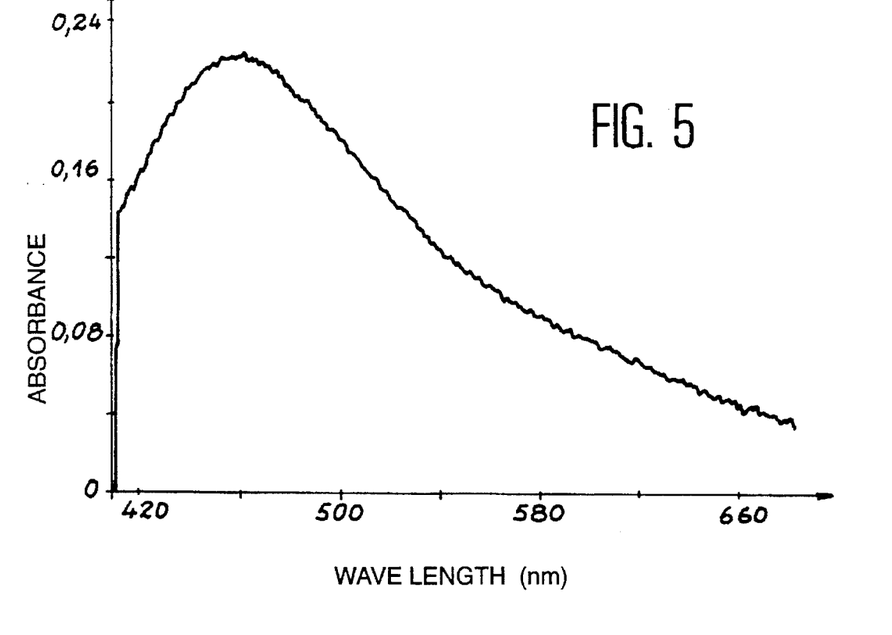
FIG. 5 The visible spectrum of a film according to the invention in the presence of nitrite ions.

FIG. 5 shows the absorption spectrum of the complex obtained under these conditions with a transparent electrode formed from a deposit of $In_2O_3$-$SnO_2$ on glass coated under the same conditions as in example 5 with a film of poly-(N-methyl pyrrole) doped by $[Fe^{III}PN_{11}O_{39}(H_2O)]^{4-}$, using a synthesis charge of 100 mC and a potential of 0.72 V.

EXAMPLE 14

This example studies the influence of the synthesis charge, i.e. the thickness of the doped polymer film, on the catalytic current obtained for the detection of the nitrite ions.

For this purpose use is made of modified electrodes obtained in examples 5 to 12 for detecting the nitrite ions following the same operating procedure as in example 13, but adding to the solution buffered to pH=4.6, 30 mmole/l of $NO_2^-$ ions. The catalytic current is then measured at −1.20 V relative to the $10^{-2}$M $Ag/Ag^+$ reference electrode, proceeding in the same way with each film of different thickness.

Figure 6:
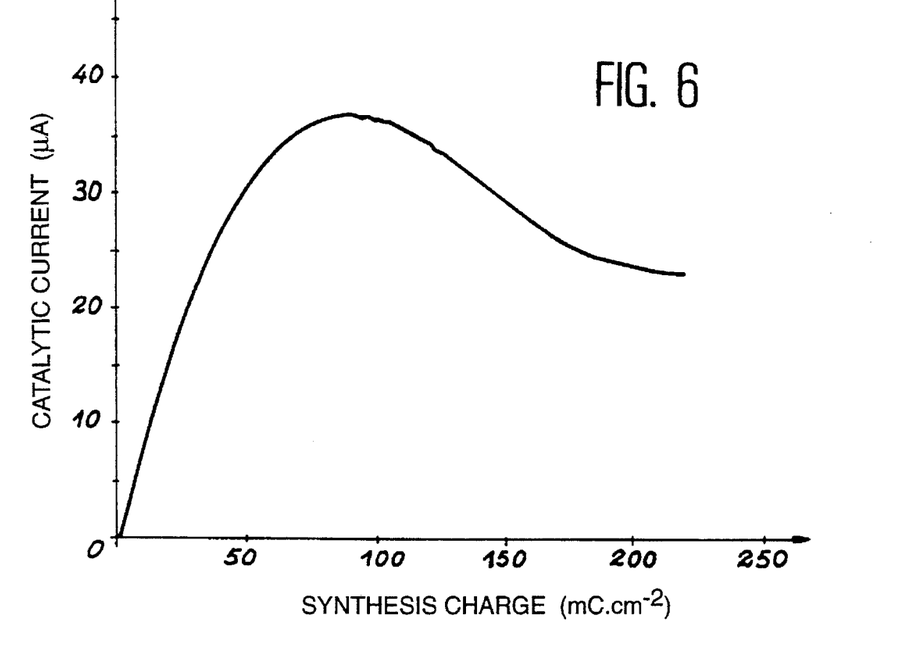
FIG. 6 A diagram representing the variation of the catalytic current (in μA) in a 30 mM $NaNO_2$ solution, as a function of the accumulated charge during the synthesis of a poly-(N-methyl pyrrole) film doped by $[Fe^{II}PW_{11}O_{35}(H_2O)]^{4-}$.

FIG. 6 gives the results obtained, i.e. the evolution of the catalytic current (in μA) as a function of the synthesis charge of the film (in $mC/cm^2$ of electrode). It can be seen that the highest catalytic current is reached for the film with the synthesis charge of 90 $mC/cm^2$ of electrode and that good results are obtained in the range 70 to 120 $mC/cm^2$ of electrode, which corresponds to thicknesses of 0.1 to 1 μm.

EXAMPLE 15

In this example preparation takes place of a vitreous carbon electrode modified by a poly-(N-methyl pyrrole) film doped by $[Fe^{III}PW_{11}O_{39}(H_2O)]^{4-}$ following the same operating procedure as in example 5 and carrying out deposition with a charge of 90 $mC/cm^2$ of electrode.

This modified electrode is then used for the detection of nitrite ions in the range $5 \cdot 10^{-5}$ to $3 \cdot 10^{-2}$ mole/l using the same operating procedure as in example 14 and measuring the catalytic current corresponding to each nitrite ion concentration.

Figure 7:
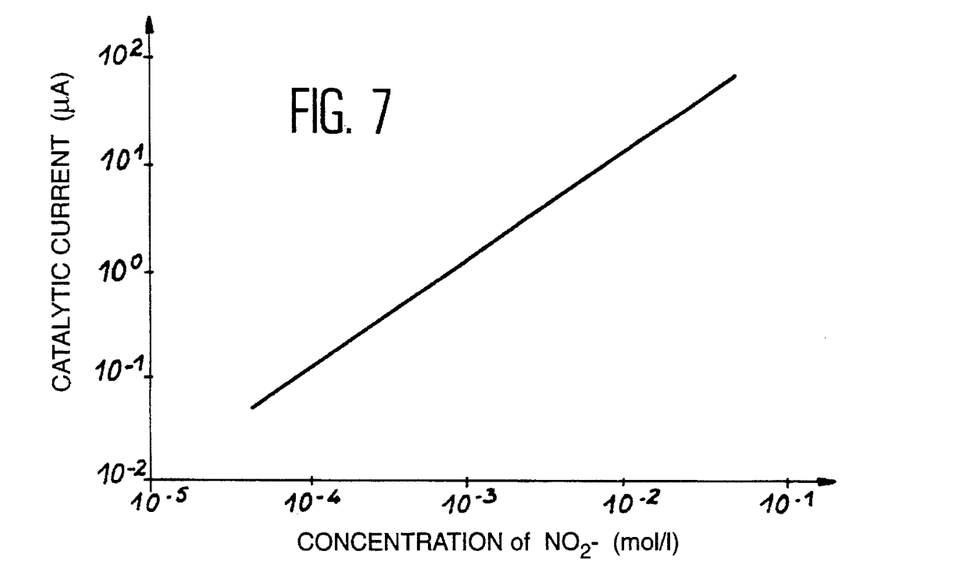
FIGS. 7 and 8 Variations of the catalytic current (in μA) as a function of the $NO_2^-$ concentration (in mole/l) obtained with two electrodes according to the invention.

FIG. 7, which shows the catalytic current (in μA) as a function of the concentration of $NO_2^-$ (in mole/l) illustrates the results obtained. It can be seen that the intensity of the catalytic current varies linearly as a function of the concentration of nitrite ions in the range $5 \cdot 10^{-5}$ to $3 \cdot 10^{-2}$ mole/l.

EXAMPLE 16

Carbon Felt Modified By a Poly-(N-Methyl Pyrrole) Film Doped By $[Fe^{III}PW_{11}O_{39}(H_2O)]^{4-}$ This example follows the operating procedure of example 5 for preparing an electrode modified by poly-(N-methyl pyrrole) doped by $[Fe^{III}PW_{11}O_{39}(H_2O)]^{4-}$, but the deposition electrode is made from carbon felt.

Thus, in this case, the deposition electrode is constituted by a carbon felt having an active electrochemical surface of 800 $cm^2$/g, i.e. 50 $cm^2/cm^3$ of felt, using a 10 mg electrode (8 $cm^2$ electrode surface) and deposition takes place by raising said carbon felt electrode to a potential of 0.60 V with respect to the $10^{-2}$M $Ag/Ag^{2+}$ electrode until 720 mC, i.e. 90 $mC/cm^2$ of electrode pass into the circuit, in order to have the highest possible catalytic activity.

This electrode is used for detecting $NO^{2-}$ ions, measuring the catalytic current under the same conditions as in example 15.

Figure 8:
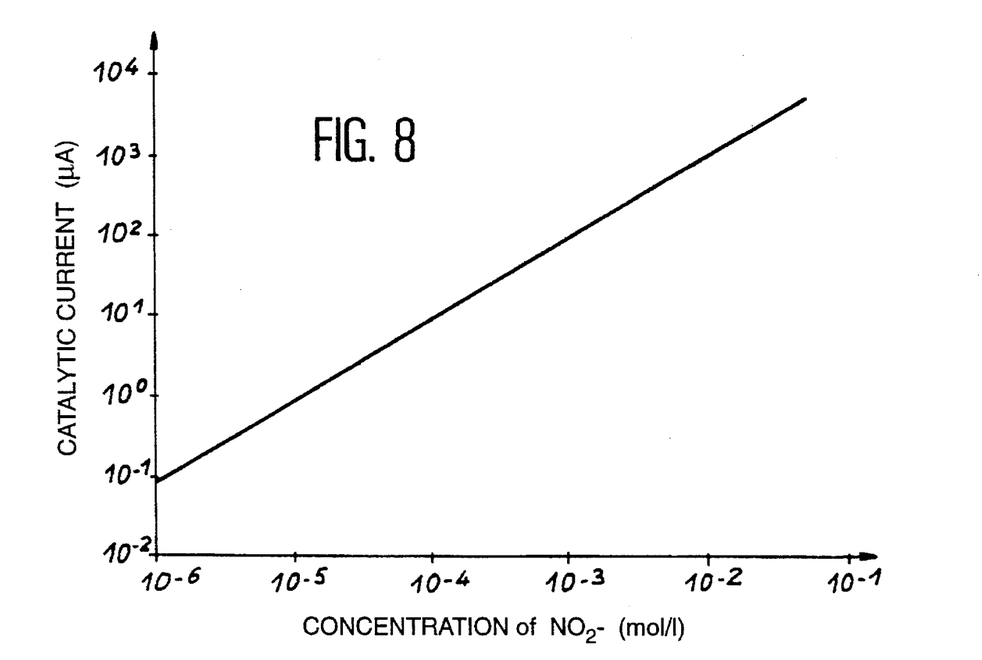

FIG. 8 gives the variations of the catalytic current intensity (in μa) as a function of the concentration of $NO_2^-$ (in mole/l) and illustrates the results obtained. It can be seen that the intensity of the catalytic current varies linearly with the $NO_2^-$ concentration in the concentration range $10^{-6}$ to $3 \cdot 10^{-2}$ mole/l.

The detection of nitrite ion concentrations up to $10^{-6}$ mole/l is particularly interesting in the medical field, where the modified electrode of example 15 is less suitable because its lower detection limit is higher ($5 \cdot 10^{-5}$ mole/l).

EXAMPLE 17

Detection of Nitrite Ions In the Presence of Nitrate Ions

This example uses the modified electrode of example 15 for detecting nitrite ions in the presence of nitrate ions, working in the same way as in example 14 and it is found that the results are not modified by the presence of nitrate ions.

The following Table 1 gives the results obtained with the modified electrodes of examples 1, 2, 15 and 16 for the detection of nitrite ions, giving the detection range and the measured catalytic currents. This table also indicates the catalytic activity (in %) of the modified electrodes taking as the reference the catalytic activity of the electrode of example 5.

This catalytic activity corresponds to the following formula:

$$\frac{I_{cat}}{I_{cat(ex\ 15)}} \times 100$$

in which $I_{cat}$ is the intensity of the catalytic current obtained with the electrode of the example in question and $I_{cat(ex\ 15)}$ is the catalytic intensity obtained with the electrode of example 15, in an aqueous solution buffered to pH=4.6 for a $NO_2^-$ concentration of $2 \cdot 10^{-2}$ mole/l.

| Ex | Polymer | Synthesis Solvent | Catalytic Activity (%) | Nitrite Detection Range (mole/l) | Catalytic Current Intensity |
|---|---|---|---|---|---|
| 1 | PPy | Acetonitrile | 43 | $10^{-4} - 3 \times 10^{-2}$ | 60 nA–19 µA |
| 5 | PPy | Water | 30 | $30 \times 10^{-4} - 3 \times 10^{-2}$ | 130 nA–12 µA |
| 15 | P(N—MePy) | Acetonitrile | 100 | $5 \times 10^{-5} - 3 \times 10^{-2}$ | 60 nA–42 µA |
| 16 | P(N—MePy) | Acetonirile | 100 | $10^{-6} - 3 \times 10^{-2}$ | 80 nA–2.7 mA |

EXAMPLE 18

Detection of Nitrogen Monoxide NO On the Basis of a Poly-(N-Methyl Pyrrole) Film Doped By $[Fe^{III}PW_{11}O_{39}(H_2O)]^{4-}$ a) Synthesis of a Vitreous Carbon Electrode Modified By a $[Fe^{III}PW_{11}O_{39}(H_2O)]^{4-}$ Film.

In this example preparation takes place of a vitreous carbon electrode (surface:0.07 cm²) modified by a poly-(N-methyl pyrrole) deposit doped by $[Fe^{III}PW_{11}O_{39}(H_2O)]^{4-}$ following the operating procedure of example 5 and making the deposit with a charge of 4 mC, i.e. 57.1 mC/cm² of electrode.

This modified electrode is washed with acetonitrile and then water for 2 minutes for each solvent. It is then immersed in 20 ml of a deaerated aqueous solution buffered to 4.6 (0.1M CH₃COOH/0.1M CH₃COONa)

Figure 9:
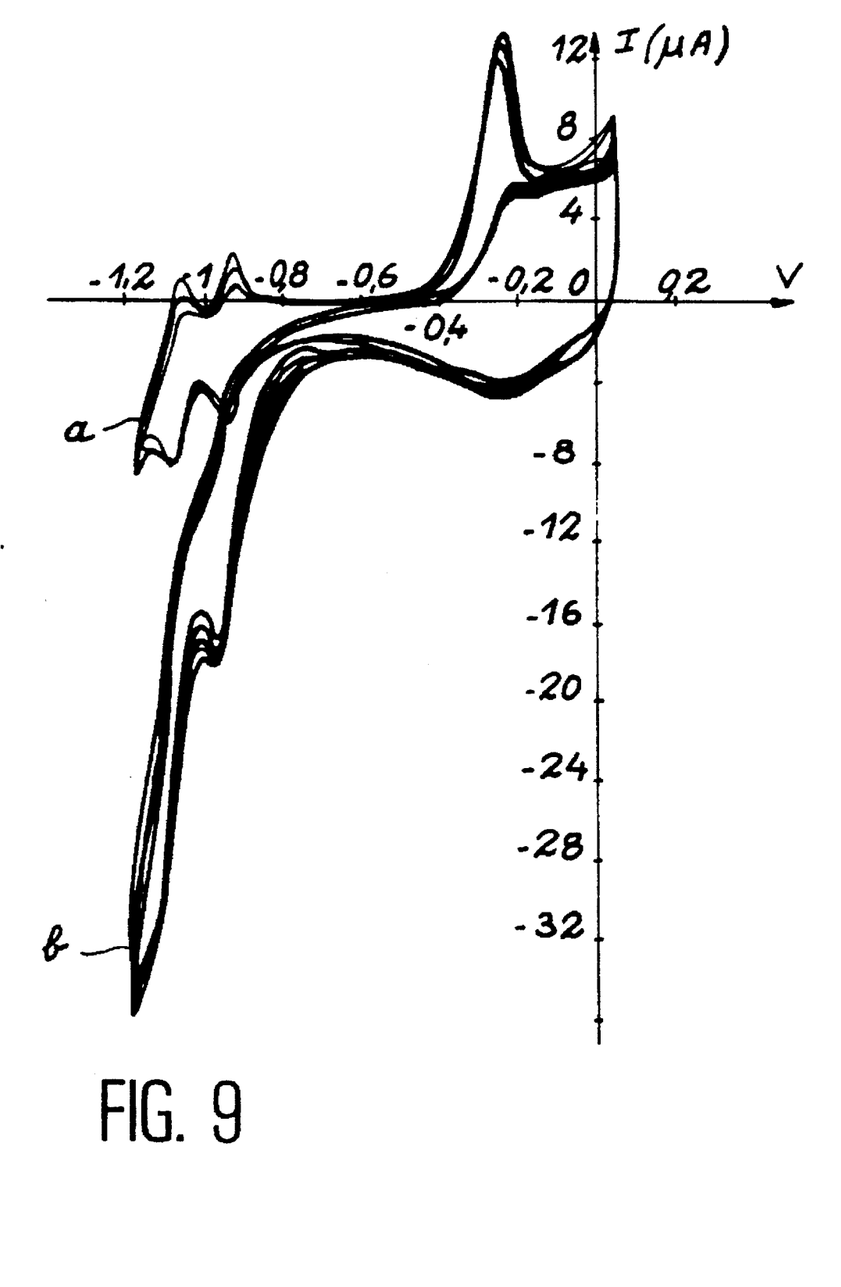
FIGS. 9 and 10 Volt-amperograms obtained at 20 mV/s (9a and 9b) and 10 mV/s (10a and 10b) during the cycling of a poly-(N-methyl pyrrole)/$Fe^{III}PW_{11}O_{39}(H_2O)]^{4-}$ film in an aqueous solution buffered to pH 4.6 (0.1M $CH_3COOH$/ 0.1M $CH_3COONa$) in the absence of NO (FIG. 9a) and after degassing the NO solution for 30 s (FIGS. 9b and 10a) and 90 s (FIG. 10b).

The successive volt-amperograms obtained at 20 mV/s in this medium between −1.20 and +0.05 V (relative to $10^{-2}$M Ag/Ag⁺) are shown in FIG. 9a and have a configuration similar to that of the volt-amperograms of FIG. 2 (example 5). It is firstly clear that the currents observed are lower because the synthesized film is thinner.

This modified electrode can be used for the electrocatalytic reduction of NO, when its electrochemical response in the buffered medium is stabilized (after 3 cycles).

b) Synthesis of Nitrogen Monoxide NO.

Nitrogen monoxide is prepared by reacting a mixture of FeCl₃, 6H₂O+H₂SO₄ 95%+H₂O (140 g; 35 ml; 30 ml) on an aqueous solution saturated with NaNO₂ (≈120 ml). The solubility of NaNO₂ is 81.5 g for 100 cm³ of water at 15° C. (Handbook of Chemistry and Physics, 62nd ed., CRC Press, Inc., 1981–1982, B-149).

This operating procedure is based on an article published recently (A. Boughriet and M. Wartel, J. Electroanal. Chem., 362 (1993) (167)).

The synthesized nitrogen monoxide is degassed in the buffered solution in which are immersed the reference electrode (Ag/Ag⁺ $10^{-2}$M) auxiliary electrode (platinum) and working electrode (vitreous carbon modified by a poly-(N-methyl pyrrole) film doped by $[Fe^{III}PW_{11}O_{39}(H_2O)]^{4-}$.

It must be ensured that everything is under an inert argon atmosphere due to the rapid reaction of NO with O₂ to form NO₂, the latter molecule reacting in turn with water to form HNO₂ and HNO₃.

c) Detection of NO.

Figure 10:
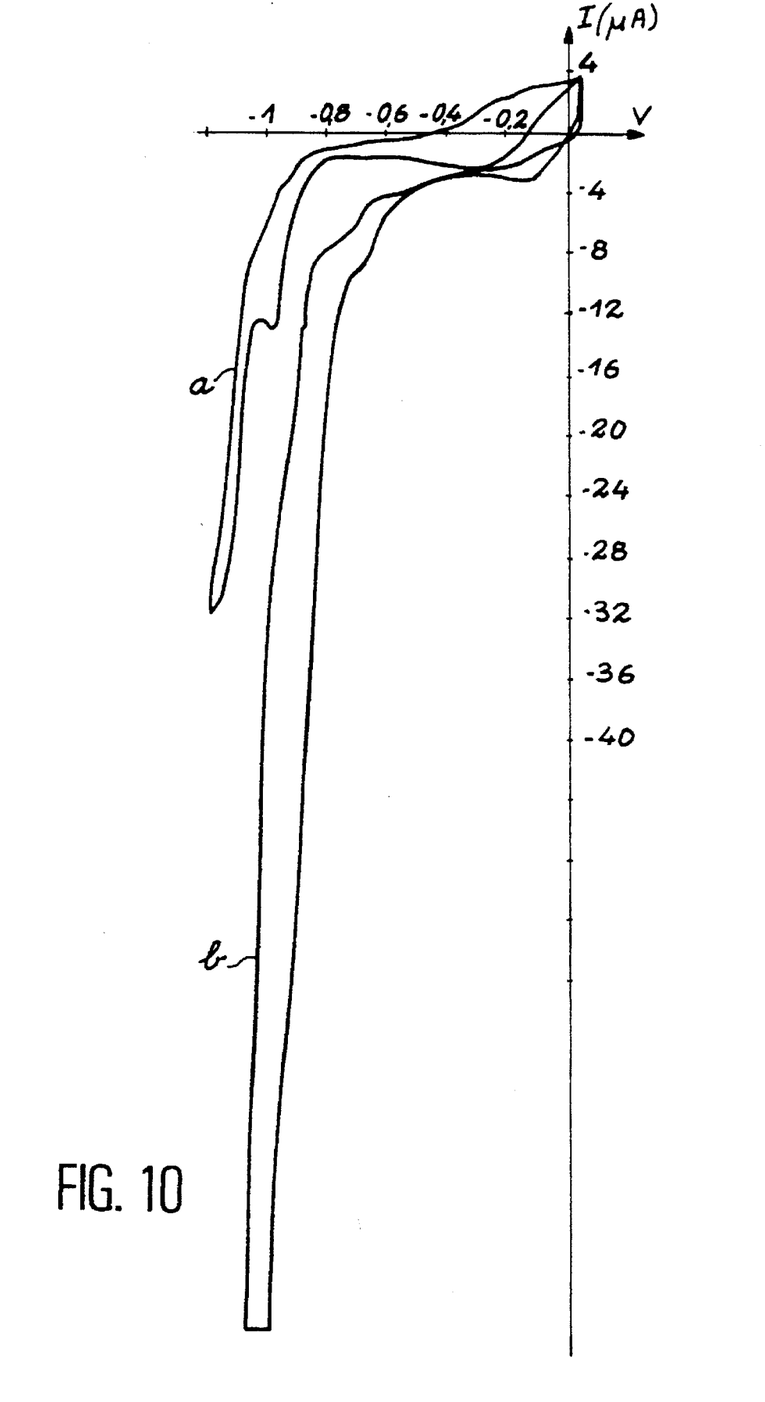
Figure 11:
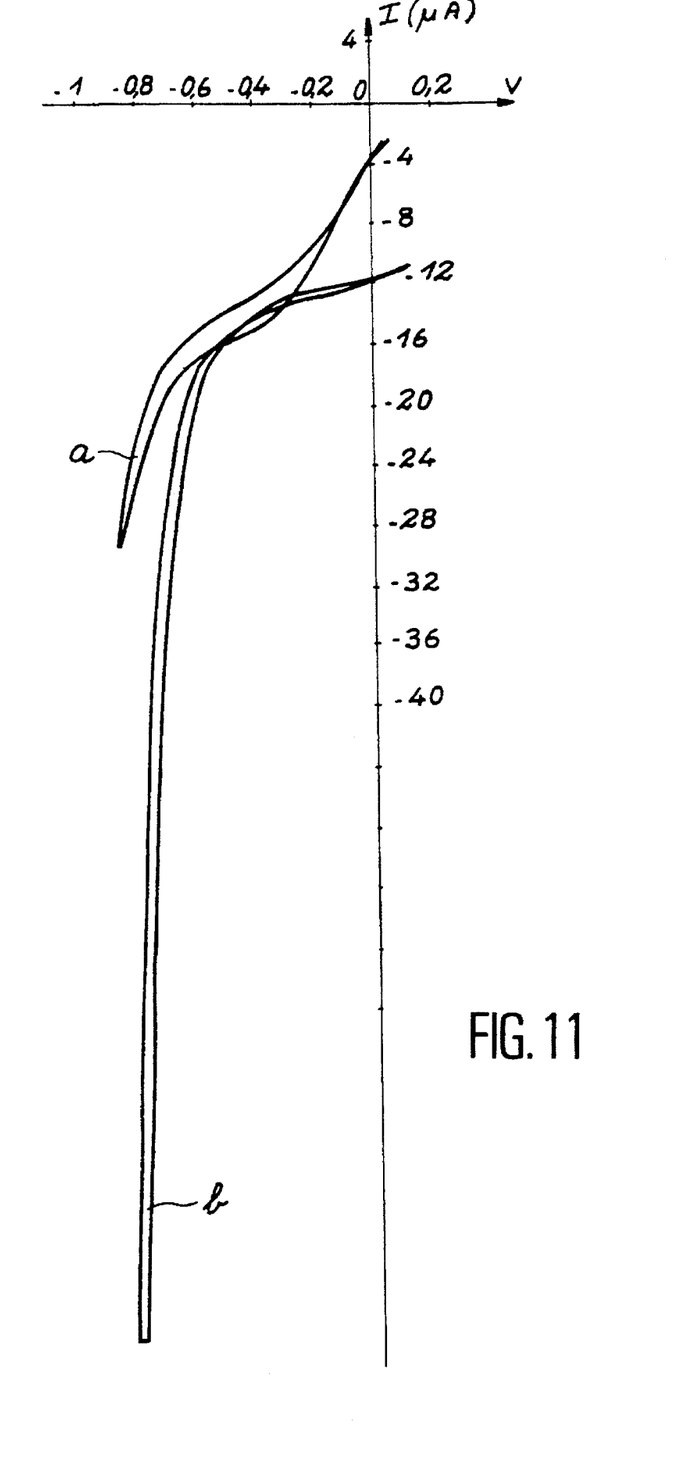
FIG. 11 The volt-amperograms obtained at 10 mV/s during the cycling of an uncovered, vitreous carbon electrode (FIG. 11a) and a vitreous carbon electrode covered by a poly-(N-methyl pyrolle)/$Fe^{III}PW_{11}O_{39}(H_2O)]^4$ film (FIG. 11b) in the solution buffered to pH 4.6 after degassing in NO for 3 min (NO-saturated solution)—the volt-amperograms being recorded at between −0.85 and +0.05 V.

After subjecting the modified electrode obtained in a) to 3 electrochemical cycles, its potential is stopped at 0 V and the nitrogen monoxide NO is degassed in the buffered solution. FIGS. 9b, 10a, 10b and 11b illustrate the volt-amperograms obtained at 20 mV/s (FIG. 9b) and 10 mV/s (FIGS. 10a, 10b and 11b) after degassing for 30 s (FIGS. 9b and 10a), 90 s (FIG. 10b) and 3 min (FIG. 11).

It can be seen that there is a significant increase in the reduction current as a function of the NO degassing time, i.e. as a function of the NO concentration.

Moreover, for a fixed NO concentration, the electrochemical response of the modified electrode is stable over several cycles (cf. FIG. 9b), which reveals the stability of the catalytic activity of the film with respect to NO reduction.

Beyond 3 min degassing, the volt-amperogram of the modified electrode remains unchanged, which means that the solution is saturated with NO. The aqueous solubility of NO is only 2 mmole/l under 1 atmosphere (The Merck Index, 9th ed., Merck & Co., Ralway, N.J., 1976, p.854).

In the presence of nitrite ions, the electroactivity of the poly-(N-methyl pyrrole)/$[Fe^{III}PW_{11}O_{39}(H_2O)]^{4-}$ film is still apparent (FIG. 4), whereas it is no longer apparent when the solution is saturated with NO (FIG. 11b).

Figure 12:
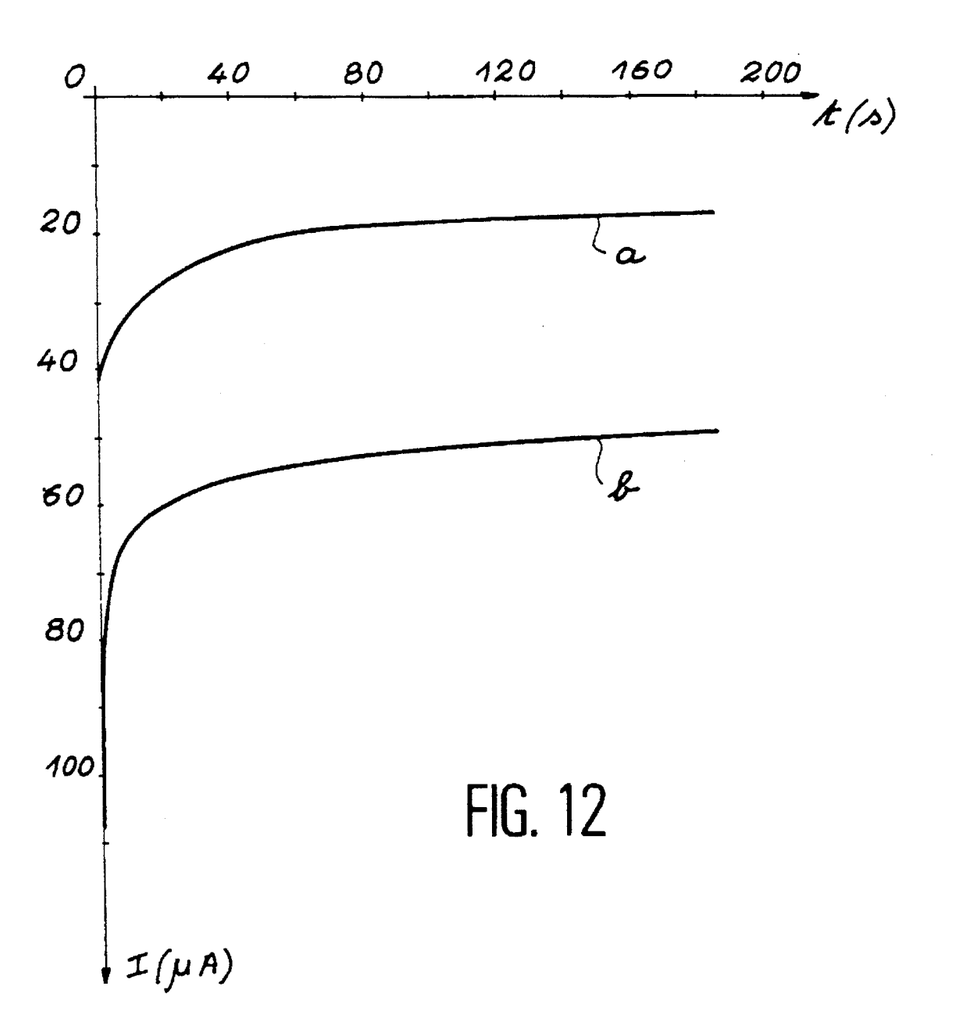
FIG. 12 Chronoamperograms i=f(t) recorded in the solution buffered to pH 4.6 and saturated with NO during electrolysis at −0.75 V of uncovered vitreous carbon electrodes (FIG. 12a) and such electrodes covered with a film of poly-(N-methyl pyrrole)/$Fe^{III}PW_{11}O_{39}(H_2O)]^4$ (FIG. 12b).

FIG. 11a shows for comparison purposes the volt-amperogram obtained with a vitreous carbon electrode not covered with the film according to the invention, whilst FIG. 12 illustrates chronoamperograms i=f(t) recorded in the solution buffered at pH 4.6 and saturated with NO during electrolysis at −0.75 V of an uncovered vitreous carbon electrode (curve a) and an electrode covered with the poly-(N-methyl pyrrole)/$[Fe^{III}PW_{11}O_{39}(H_2O)]^{4-}$ of said example (curve b).

Thus, on an uncovered vitreous carbon electrode (FIG. 11a), the reduction potential of NO to $NH_4^+$ is higher than that of $NO_2^-$ to $NH_4^+$.

In the scanned potential range (−1.20 to +0.05 V), the current due to the catalytic reduction of NO to $NH_4^+$ ions rapidly exceeds that due to the electroactivity of the film (poly-N-methyl pyrrole matrix) and electroactive sites of the immobilized catalyst. As the measured total current is the sum of these two currents, the recorded volt-amperograms reveal the progressive disappearance of the electrochemical response of the film when the NO concentration in the solution increases.

Nevertheless for certain applications and in particular biomedical applications, the nitrogen monoxide to be detected is present at a concentration well below the solubility limit, so that the electroactivity of the film in the presence of this molecule will remain apparent.

Moreover, it is not necessary to detect NO at an excessively negative potential as in the case of the detection of $NO_2^-$ (at −1.20 V). Thus, by fixing the potential at 0.75 V, the measured reduction current is proportional to the NO concentration in the case of the electrode modified by a poly-(N-methyl pyrrole)/$[Fe^{III}PW_{11}O_{39}(H_2O)]^{4-}$ film (FIG. 12b), whereas it is independent thereof in the case of the uncovered vitreous carbon electrode (FIG. 12a).

From a reaction standpoint, the mechanism given for the electrocatalytic reduction of $NO_2^-$ is valid for that of NO. Thus, NO reacts in the same way as $NO_{2-}$ with the reduced form of the catalyst immobilized in the $[Fe^{III}PW_{11}O_{39}(H_2O)]^{5-}$ film in order to form a nitrosyl complex

[Fe$''$PW$_{11}$O$_{39}$(NO)]$^{5-}$ detectable at an identical wavelength (465 nm) to that of the nitrosyl complex formed from NO$_2^-$ (cf. example 13).

We claim:

1. A process for amperometric detection of nitrite ions, nitrogen monoxide or a substance containing a NO group present in a sample, which comprises the steps of:

providing a sensor having a first electrode, a second auxiliary electrode, and a third reference electrode that are immersed in an aqueous solution contained in an enclosure, introducing the sample into the aqueous solution, applying a potential between the first and third electrodes, and measuring the electric current flowing between the first and second electrodes, wherein the first electrode comprises an electrically conductive support coated with an electronically conductive polymer film doped by mixed heteropolyanions complying with one of the formulas:

[M$'''$X$^1$W$_{11}$O$_{39}$(H$_2$O)]$^{n-}$ and

[M$'''$X$^2_2$W$_{17}$O$_{61}$(H$_2$O)]$^{7-}$ in which M represents Fe, Rh, Al, Ga, In or Tl, X$^1$ represents P or As and is equal to 4, X$^1$ represent Si or Ge and n is equal to 5, or X$^1$ represents B and n is equal to 6, and X$^2$ represents P or As, provided that X$^1$ does not represent Si when M represents Fe and wherein the mixed heteropolyanions catalyze the reduction of the nitrite ions, nitrogen monoxide or a substance containing a NO group.

2. The process according to claim 1, wherein the aqueous solution is a buffered medium having a pH of approximately 4.6.

3. The process according to claim 1 characterized in the conductive polymer is poly-(N-methyl pyrrole).

4. A process according to claim 1, wherein the electronically conductive polymer film comprises a polymer selected from pyrrole, thiophene, aniline and their derivatives.

5. A process according to claim 4, characterized in that the electronically conductive polymer film comprises polypyrrole or a poly-(N-alkyl pyrrole).

6. A process according to claim 1, wherein the mixed heteropolyanion is [Fe$'''$PW$_{11}$O$_{39}$(H$_2$O)]$^{4-}$.

7. A process according to claim 1 wherein the polymer film has a thickness of 0.1 to 1 μm.

8. A process according to claim 1, wherein the polymer film contains 0.06 to 0.08 of mixed heteropolyanion per monomer unit.

9. A process according to claim 1, wherein the second electrode is a platinum electrode.

10. A process according to claim 1, wherein the conductive support of the first electrode is made from vitreous carbon or carbon felt.

* * * * *